(12) United States Patent  
Benneker et al.

(10) Patent No.: US 6,900,327 B2
(45) Date of Patent: *May 31, 2005

(54) 4-PHENYLPIPERIDINE COMPOUNDS

(75) Inventors: Franciscus Bernardus Gemma Benneker, Nijmegen (NL); Frans Van Dalen, Nuenen (NL); Jacobus Maria Lemmens, Mook (NL); Theodorus Hendricus Antonium Peters, Arnhem (NL); Frantisek Picha, Brno (CZ)

(73) Assignee: Synthon BCT Technologies, LLC, Chapel Hill, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/855,710

(22) Filed: May 16, 2001

(65) Prior Publication Data

US 2001/0031767 A1 Oct. 18, 2001

Related U.S. Application Data

(62) Division of application No. 09/200,743, filed on Nov. 30, 1998, which is a division of application No. 08/872,023, filed on Jun. 10, 1997, now Pat. No. 5,874,447.

(51) Int. Cl.⁷ ..................... C07D 405/12; A61K 31/445
(52) U.S. Cl. ....................... 546/197; 514/321
(58) Field of Search ............ 546/197; 514/321

(56) References Cited

U.S. PATENT DOCUMENTS

| | | | |
|---|---|---|---|
| 3,912,743 A | 10/1975 | Christensen et al. | 546/197 |
| 4,007,196 A | 2/1977 | Christensen et al. | 546/197 |
| 4,585,777 A | 4/1986 | Lassen et al. | 514/317 |
| 4,721,723 A | 1/1988 | Barnes et al. | 514/321 |
| 4,902,801 A | 2/1990 | Faruk et al. | 546/220 |
| 4,985,446 A | 1/1991 | Drejer | 514/321 |
| 5,258,517 A | 11/1993 | Zepp et al. | 546/240 |
| 5,276,042 A | 1/1994 | Crenshaw | |
| 5,371,092 A | 12/1994 | Johnson | 514/321 |
| 5,637,601 A | 6/1997 | Hammer et al. | 514/327 |
| 5,668,134 A | 9/1997 | Klimstra et al. | 514/254 |
| 5,672,609 A | 9/1997 | Bryant | 514/318 |
| 5,872,132 A * | 2/1999 | Ward et al. | 514/321 |
| 6,063,927 A | 5/2000 | Craig et al. | 546/197 |

FOREIGN PATENT DOCUMENTS

| | | |
|---|---|---|
| AU | 99 678 B | 9/1988 |
| CA | 2143070 | 8/1995 |
| CA | 2187128 | 6/1997 |
| DE | 2404113 C2 | 8/1974 |
| DE | 19603797 A1 | 8/1996 |
| EP | 0 188 081 A2 | 7/1986 |
| EP | 0 190 496 A2 | 8/1986 |
| EP | 190496 | 8/1986 |
| EP | 0 219 934 A1 | 4/1987 |
| EP | 0 223 334 A1 | 5/1987 |
| EP | 0 223 403 A2 | 5/1987 |
| EP | 0 266 574 A2 | 5/1988 |
| EP | 0 269 303 A2 | 6/1988 |
| EP | 0 300 617 A1 | 1/1989 |
| EP | 0 374 674 A2 | 6/1990 |
| EP | 0 374 675 A2 | 6/1990 |
| EP | 0 600 714 A1 | 6/1994 |
| EP | 0 714 663 A2 | 6/1996 |
| EP | 0 802 185 A1 | 10/1997 |
| EP | 0 810 224 A1 | 12/1997 |
| EP | 0 812 827 A1 | 12/1997 |
| GB | 1 422 263 | 1/1976 |
| GB | 2297550 | 8/1996 |
| NL | 179187 | 8/1974 |
| WO | WO 92/09281 | 6/1992 |
| WO | WO 93/22284 | 11/1993 |
| WO | WO 94/03428 | 2/1994 |
| WO | WO 95/15155 | 6/1995 |
| WO | WO 95/16448 | 6/1995 |
| WO | WO 95/20964 | 8/1995 |
| WO | WO 96/24595 | 8/1996 |
| WO | WO 96/31197 | 10/1996 |

(Continued)

Primary Examiner—Celia Chang
(74) Attorney, Agent, or Firm—Mark R. Buscher

(57) ABSTRACT

The invention relates to a compound, and pharmaceutically acceptable salts, having the formula I:

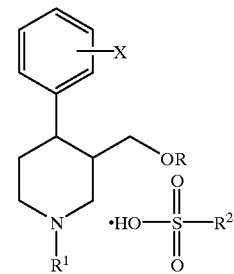

wherein:

R represents an alkyl or alkynyl group having 1–4 carbon atoms, or a phenyl group optionally substituted by $C_{1-4}$ alkyl, alkylthio, alkoxy, halogen, nitro, acylamino, methylsulfonyl or methylenedioxy, or represents tetrahydronaphthyl, $R^1$ represents hydrogen, trifluoro ($C_{1-4}$) alkyl, alkyl or alkynyl, X represents hydrogen, alkyl having 1–4 carbon atoms, alkoxy, trifluoroalkyl, hydroxy, halogen, methylthio or aralkoxy, $R^2$ represents:
  a C1–C10 alkyl group,
  a phenyl group optionally substituted by one or more of the following groups:
    a C1–C10 alkyl group,
    a halogen group,
    a nitro group,
    hydroxy group,
    and/or an alkoxy group.

3 Claims, No Drawings

FOREIGN PATENT DOCUMENTS

| | | |
|---|---|---|
| WO | WO 96/36636 | 11/1996 |
| WO | WO 97/03670 | 2/1997 |
| WO | WO 97/18798 | 5/1997 |
| WO | WO 97/24323 | 7/1997 |
| WO | WO 97/31915 | 9/1997 |
| WO | WO 98/01424 | 1/1998 |

* cited by examiner

4-PHENYLPIPERIDINE COMPOUNDS

This application is a divisional under 35 U.S.C. 120 of prior U.S. patent application Ser. No. 09/200,743, filed Nov. 30, 1998, the entire contents of which are incorporated herein by reference, which is in turn a divisional under 35 U.S.C. 120 of prior U.S. patent application Ser. No. 08/872,023, filed Jun. 10, 1997, now U.S. Pat. No. 5,874,447, the entire contents of which are incorporated herein by reference.

The present invention relates to a group of tri-substituted, 4-phenylpiperidines, to a process for preparing such compounds, to a medicament comprising such compounds, and to the use of such compounds for the manufacture of a medicament.

The compound paroxetine, trans-4-(4'-fluorophenyl)-3-(3',4'-methylene dioxyphenoxymethyl)piperidine having the formula below:

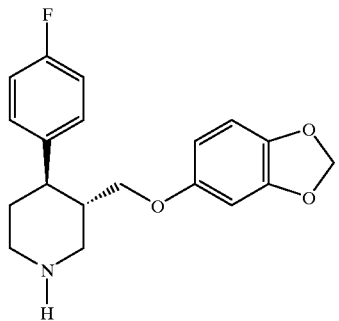

is known and has been used in medicaments for treating, amongst other ailments, depression.

Paroxetine has been used as a therapeutic agent in the form of a salt with pharmaceutically acceptable acids. The first clinical trials were conducted with the acetate salt.

A known useful salt of paroxetine is the hydrochloride. This salt is considered to be the active substance in several marketed pharmaceutical products, e.g. Paxil or Seroxat. A number of forms of paroxetine hydrochloride have been described:

the anhydrous form in several crystalline modifications (PCT Appl. WO 96/24595);

the hydrated form—a hemihydrate (EP 223403) and in the solvated forms.

The comparison of behaviour between anhydrous and hydrated form of paroxetine hydrochloride is described in the Intl. Journal of Pharmaceutics, 42, 135–143 (1988).

EP 223403 discloses paroxetine hydrochloride hemihydrate and pharmaceutical compositions based thereon.

Most of these known salts of paroxetine have unsuitable physico-chemical characteristics for ensuring safe and efficient handling during production thereof and formulation into final forms, since they are unstable (acetate, maleate) and possess undesirable hygroscopicity.

Furthermore their formation by crystallization from both aqueous or non-aqueous solvents is generally low-yielded and troublesome as they usually contain an undefined and unpredicted amount of bound solvent which is difficult to remove.

The crystalline paroxetine hydrochloride hemihydrate approaches these problems, but as stated in WO 95/16448, its limited photostability causes undesired colouration during classical wet tabletting procedure.

Moreover, crystalline paroxetine hydrochloride hemihydrate exhibits only limited solubility in water.

It has been generally suggested that where the aqueous solubility is low, for example less than 3 mg/ml, the dissolution rate at in vivo administration could be rate-limiting in the absorption process. The aqueous solubility of the paroxetine hemihydrate at room temperature exceeds this threshold by a relatively small margin.

An object of the present invention is to provide a compound with improved characteristics.

According to a first aspect, the present invention comprises a compound, and pharmaceutically acceptable salts, having the formula I:

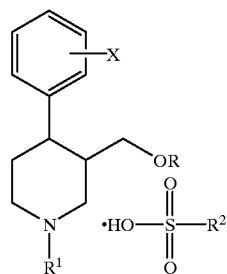

R represents an alkyl or alkynyl group having 1–4 carbon atoms, or a phenyl group optionally substituted by $C_{1-4}$ alkyl, alkylthio, alkoxy, halogen, nitro, acylamino, methylsulfonyl or methylenedioxy, or represents tetrahydronaphthyl, $R^1$ represents hydrogen, trifluoro ($C_{1-4}$) alkyl, alkyl or alkynyl, X represents hydrogen, alkyl having 1–4 carbon atoms, alkoxy, trifluoroalkyl, hydroxy, halogen, methylthio or aralkoxy, $R^2$ represents:
  a C1–C10 alkyl group,
  a phenyl group optionally substituted by one or more of the following groups:
    a C1–C10 alkyl group,
    a halogen group,
    a nitro group,
    hydroxy group,
    and/or an alkoxy group.

The inventors have found that these compounds exhibit good stability and very high solubility. This yields the advantage that high concentrations of the compound are obtainable in small volumes.

The R group is preferably the 3,4 methylenedioxyphenyl group of the formula:

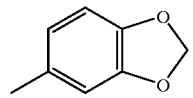

The X group is preferably a fluorine group attached to position 4 in the phenyl ring.

The $R^2$ group preferably represents a C1–C4 alkyl group, and most preferably represents a C1–C2 alkyl group in order to provide an optimum solubility.

The compounds can have a solubility at about 20° C. of at least about 10 mg/ml water, preferably having a solubility in water of at least 100, for example 500 and most preferably of at least 1000 mg/ml water.

According to a second aspect of the present invention, there is provided a process for preparing a compound as above, comprising the steps of mixing together a 4 phenylpiperidine compound, a salt and/or a base thereof having the formula II:

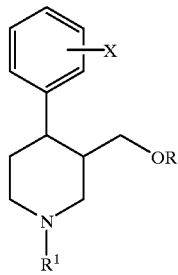

wherein:
R represents an alkyl or alkynyl group having 1–4 carbon atoms, or a phenyl group optionally substituted by $C_{1-4}$ alkyl, alkylthio, alkoxy, halogen, nitro, acylamino, methylsulfonyl or methylenedioxy, or represents tetrahydronaphthyl,
$R_1$ represents hydrogen, trifluoro ($C_{1-4}$) alkyl, alkyl or alkynyl,
X represents hydrogen, alkyl having 1–4 carbon atoms, alkoxy, trifluoroalkyl, hydroxy, halogen, methylthio or aralkoxy,
with a sulfonic acid of the general formula $R_2$—$SO_3H$, wherein $R_2$ represents:
 a C1–C10 alkyl group,
 a phenyl group optionally substituted by one or more of the following groups:
  a C1–C10 alkyl group,
  a halogen group,
  a nitro group,
  a hydroxy group, and/or
  an alkoxy group,
to form a solution, followed by separating the compound formed from this solution.

The compounds of the invention can be prepared from the free base of the 4 phenylpiperidine, having the formula II, this preferably being paroxetine, by treatment with a sulfonic acid as defined above in a suitable solvent to form a solution of the desired acid addition salt, whereafter this is precipitated out of the solution.

The equation for paroxetine free base and sulfonic acids is as follows:

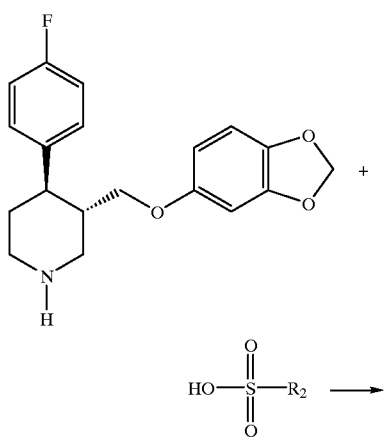

The forming of a solution may preferably proceed at temperatures from about 0° C. to the boiling point of the solvent.

Optionally, the solution may be purified by treatment of activated charcoal, silica gel, kieselguhr or other suitable materials.

Alternatively, the solution of a salt of the invention can be formed by dissolution of a salt of 4 phenyl piperidine having the formula II with an organic sulfonic acid.

For example the compounds of the invention may be prepared from a paroxetine C1–C5 carboxylate, such as the acetate, by addition of corresponding organic sulfonic acid to the solution of the said carboxylate, as follows:

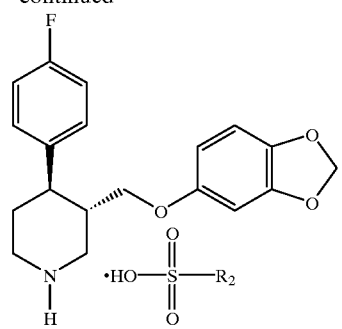

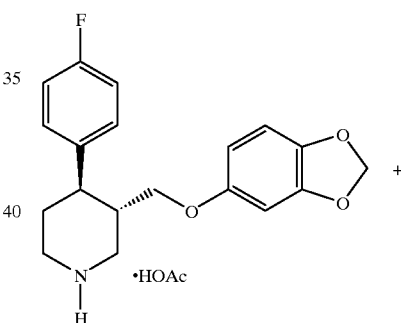

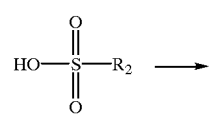

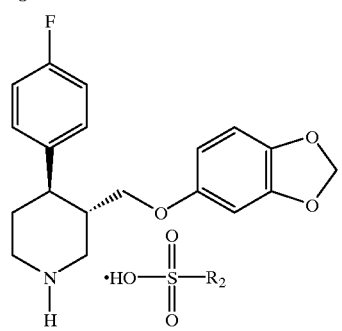

According to a third aspect of the present invention, there is provided a compound obtainable by this process.

According to a fourth aspect of the present invention there is provided the above compound for use as a medicament and, according to a fifth aspect, a medicament comprising this compound, and to the use thereof for treating depressions, obsessive compulsive disorders, panic disorders, bulimia, anorexia, pain, obesity, senile demential, migraine, anorexia, social phobia, depressions arising from pre-menstrual tension.

According to a sixth aspect of the present invention, there is provided the use of a compound of the invention as a reagent in further syntheses. More specifically, the compounds of the present invention can be used as a start reagent for forming further acid addition salts, for example for providing further paroxetine acid addition salts, by reacting with a suitable reagent, i.e. with a corresponding acid. For example, the formation of paroxetine maleate according to the present invention proceeds by the following equation:

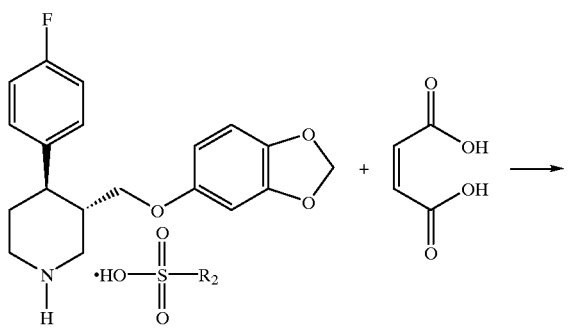

and the formation of paroxetine acetate proceeds as follows:

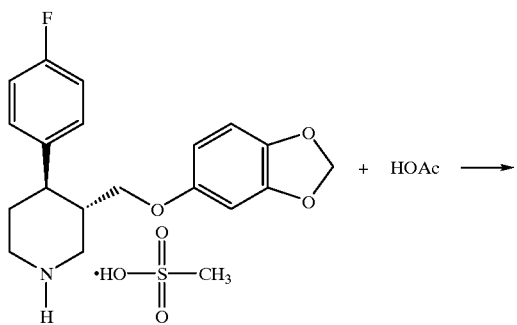

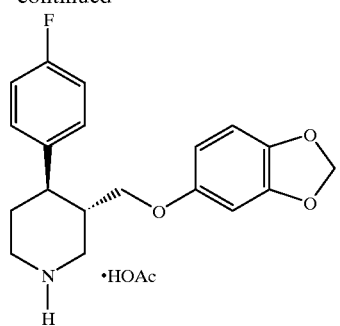

This is an advantageous route, since by using the substantially pure sulfonic acid salts according to the present invention as a start reagent, the preparation of a further salt, as above, results in this further salt having a high purity. The inventors have shown that such salts have a surprisingly high purity.

Similarly, the compounds of the present invention can react with a base, such as an inorganic and/or an organic base, to form (liberate) free bases of the corresponding compounds. As exemplified on paroxetine, the reaction proceeds according to the equation:

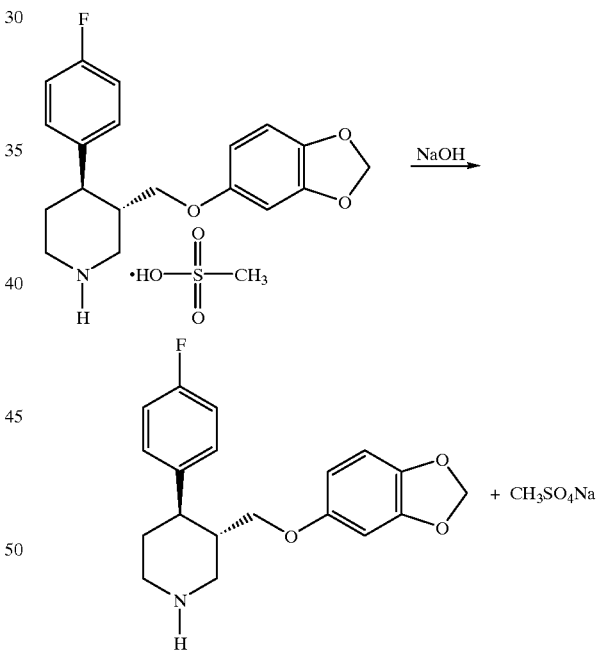

The free bases liberated from the compounds of the present invention have surprisingly higher purity than if prepared by known methods which is especially important in case of their use for production of pharmaceuticals.

Accordingly, the new compounds of the first aspect of the invention can also form hydrates and/or solvates by a contact with a corresponding reaction partner, i.e. with water and/or with a solvent. Examples of such further salts, hydrates and solvates, for example these of paroxetine, are the:

| | | |
|---|---|---|
| hydrochloride | oxalate | dihydrate |
| hydrobromide | succinate | trihydrate |
| hydroiodide | tartrate | hexahydrate |
| acetate | citrate | methanolate |
| propionate | embonate | ethanolate |
| maleate | hemihydrate | |
| fumarate | hydrate | |

The inventors have shown that such salts have a surprisingly high purity.

Examples of bases which can be employed in the preparation of the free bases are: sodium hydroxide, potassium hydroxide, calcium hydroxide, ammonium hydroxide, sodium carbonate, methylamine, dimethylamine, triethylamine, pyridine and such like.

Since the compounds according to the present invention exhibit high solubility, they can be dosed, for example injected, in a high concentration, low volume solution, this method of dosing being particularly advantageous with certain patients, such as manic depressives and such like, i.e. patients who are unable or unwilling to swallow medicine.

The compounds of the present invention can be formulated into various types of pharmaceutical compositions for treatment of humans and animals. Pharmaceutical compositions according to the present invention comprise a compound of the invention alone or together with a pharmaceutically acceptable carrier or diluent. The preferred formulations are those for oral administration (tablets, capsules) but formulations for parenteral or topical administration are also within the scope of the invention. The high water solubility of the compounds of the invention enables high dissolution rates in solid dosage forms based on the compounds of the invention to be obtained, during the in vitro release as well as good bioavailability after peroral application in vivo.

The tablets containing compounds of the present invention can be prepared both by tabletting procedure in which water is present (e.g. aqueous granulation) as well as by tabletting processing it which water is absent (direct compression, dry granulation) and may be coated by any suitable means of coating.

The present invention will now be further elucidated by way of the following examples and results.

EXPERIMENTAL

A seeding crystal of paroxetine methane sulfonate was made as follows:
2.7 g (8.2 mmol) of paroxetine was dissolved in
15 ml of hot ethanol.
1.0 g (10.4 mmol) of methanesulfonic acid in
15 ml of ethanol was added and the mixture was cooled to room temperature. When the mixture had reached room temperature the mixture was put in the freezer at −20° C. overnight. No crystal line compound was obtained.
The mixture was evaporated to dryness leaving an oil.
After 1 month at room temperature a waxy solid was obtained. Part of this solid was taken apart and the rest was dissolved in
10 ml of EtOAc. The waxy crystals were added and the mixture was put in the freezer at −20° C. overnight. A white crystalline product was precipitated. After filtration and drying in a vacuumoven
2.5 g (5.9 mmol) of paroxetine methane sulfonate was obtained.
Yield 72%
This seeding crystal was subsequently used in following examples 1 and 3.

EXAMPLES

Example 1

Paroxetine Methane Sulfonate from Paroxetine

To a solution of 43.5 g (132 mmol) of paroxetine, prepared by the procedure disclosed in U.S. Pat. No. 4,007,196, 12.7 g (132 mmol) of methane sulfonic acid was added to 150 ml of boiling ethyl acetate. The mixture was left at room temperature for 2 hours. Subsequently the mixture was placed overnight at −20° C., with a seeding crystal. The obtained solid was filtered off and washed with
50 ml of ether. The obtained white solid was dried overnight in a vacuumoven.
47.1 g (111 mmol) of product
Yield 99.5%
Analytical characterization of the compound obtained is shown in Table 1. The purity of the compound obtained was 98% (HPLC).

Example 2

Paroxetine Benzene Sulfonate from Paroxetine
3.8 g (11.5 mmol) of paroxetine was dissolved in
10 ml of hot ethylacetate.
1.82 g (11.5 mmol) of anhydrous benzenesulfonic acid was added. The mixture was left at room temperature for 2 h. The mixture was evaporated to dryness and dissolved in dichloromethane, and evaporated again to dryness leaving an oil. This oil was solidified through high vacuum (0.1 mmHg) evaporation leaving
5.0 g (1.3 mmol) of an off white solid. To this solid was added
5 ml of acetone and the suspension was stirred for 5 minutes during which a white suspension was obtained. The solid was filtered off and dried under vacuum.
4.8 g (9.9 mmol) of product was obtained.
Yield 85%
Analytical characterization of the compound obtained is shown in Table 1. The purity of the compound obtained was 99.4% (HPLC).

Example 3

Paroxetine p-toluene Sulfonate from Paroxetine
5.0 g (15 mmol) of paroxetine was dissolved in
25 ml of hot ethylacetate.
2.9 g (15 mmol) of p-toluenesulfonic acid was added. The mixture was left at room temperature for 2 h and subsequently put in the freezer, with a seeding crystal, for 14 h. The solid was filtered off and washed once with
10 ml of n-hexane. The obtained white solid was dried overnight in a vacuumoven.
4.8 g (10 mmol) of a white solid was obtained.
Yield 67%
Analytical characterization of the compound obtained is shown in Table 1. The purity of the compound obtained was 99.4% (HPLC).

Example 4

Paroxetine p-chlorobenzene Sulfonate from Paroxetine
1.1 g (3.3 mmol) of paroxetine was dissolved in
3 ml of hot ethylacetate.
0.76 g (3.3 mmol) of 90% p-chlorobenzenesulfonic acid was added. The mixture was left at room temperature for 1 h and washed with
5 ml of water. The organic layer was dried with $Na_2SO_4$, filtered and evaporated to dryness leaving 1.5 g (2.9 mmol) of an off white solid.
Yield 88%
Analytical characterization of the compound obtained is shown in Table 1. The purity of the compound obtained was 99.4% (HPLC)

Example 5
Paroxetine Maleate from Paroxetine Methane Sulfonate 1.0 g (2.4 mmol) of paroxetine methane sulfonate in
5 ml of hot water. To this solution was added
0.32 g (2.8 mmol) of maleic acid. The mixture was placed at 4° C. overnight after which a solid with a yellow oil was precipitated on the bottom of the flask. The solid/oil was filtered off and washed 3 times with
10 ml of ether and dried in a vacuumoven.
0.8 g (2.0 mmol) off white crystals were obtained
Yield 85%
The purity of the compound obtained was 99.5% (HPLC).

Example 6
Paroxetine Acetate from Paroxetine Methane Sulfonate 1.0 g (2.4 mmol) of paroxetine methane sulfonate in
5 ml of hot iso-propanol. To this solution was added
0.2 g (3.2 mmol) of acetic acid. The mixture was placed at 4° C. overnight after which a solid was precipitated. The solid was filtered off and washed 3 times with
10 ml of ether and dried in a vacuumoven.
0.5 g (1.3 mmol) off white crystals were obtained
Yield 54%
The purity of the compound obtained was 99.5% (HPLC).

Example 7
Paroxetine Free Base from Paroxetine Methane Sulfonate 10.0 g (24.0 mmol) of paroxetine methane sulfonate in
150 ml of water and
200 ml of ethyl acetate. To this was added
12.4 g (31 mmol) of an aqueous 10 wt % NaOH solution and the suspension was stirred for 15 minutes.
The layers were separated and the aqueous layer was extracted once with
50 ml of ethyl acetate. The combined organic layers are washed once with
100 ml of water and dried over $Na_2SO_4$. The $Na_2SO_4$ was filtered off and washed once with
50 ml of ethyl acetate. The ethyl acetate was evaporated off, leaving
7.5 g (22.8 mmol) of an oily product.
Yield 95%
The purity of the compound obtained was 99.5% (HPLC).
A number of the compounds obtained were analysed, the results being shown in tables 1–5 below:

TABLE 1

Characterization of salts of paroxetine with certain organic sulfonic acids R-$SO_3$H R = $CH_3$-(paroxetine methane sulfonate):

m.p.: 142°–144° C.
DSC curve (closed pan, 10° C./min): onset 145.8° C., 79.0 J/g.
IR spectrum (KBr, in cm$^{-1}$): 531, 546, 777, 838, 931, 962, 1038, 1100, 1169, 1208, 1469, 1500, 1515, 1615, 2577, 2869, 2900, 3023.
1H-NMR (ppm): 1.99 (br d, $H_{5eq}$, 1H); 2.27 (ddd, $H_{5ax}$, 1H); 2.48–2.65 (m, $H_3$, 1H); 2.82–2.92 (m, $H_4$, $CH_3$, 4H); 2.95–3.20 (m, $H_{2ax}$, $H_{6ax}$, 2H); 3.47 (dd, $H_7$, 1H); 3.58–3.74 (m, $H_{2eq}$, $H_{6eq}$, $H_7$, 3H); 5.88 (s, $H_{7''}$, 2H); 6.10 (dd, $H_{6''}$, 1H); 6.33 (d, $H_{2''}$, 1H); 6.61 (d, $H_{5''}$, 1H); 7.09 (dd, $H_{3'}$, $H_{5'}$, 2H); 7.22 (dd, $H_{2'}$, $H_{6'}$, 2H); 8.85 (br d, $NH_{eq}$, 1H); 9.11 (br d, $NH_{ax}$, 1H).

TABLE 1-continued

Characterization of salts of paroxetine with certain organic sulfonic acids R-$SO_3$H 13C-NMR (ppm): 30.0 (s, $C_5$); 39.3 (s, $C_3$); 39.5 (s, $C_4$); 41.7 (s, SC); 44.6 (s, $C_6$); 46.8 (s, $C_2$); 67.4 (s, $C_7$); 97.8 (s, $C_{2''}$); 101.2 (s, $C_{7''}$); 105.4 (s, $C_{6''}$); 107.8 (s, $C_{5''}$); 115.8 (d, $C_{3'}$, $C_{5'}$); 128.4 (s, $C_6$, $C_{2'}$); 137.1 (s, $C_{4'}$); 142.0 (s, $C_1$); 148.2 (s, $C_{3''}$); 153.7 (s, $C_{1''}$); 161.9 (d, $C_{4'}$).

R = $C_6H_5$-(paroxetine benzene sulfonate):

mp.: 55°–60° C.
IR spectrum (KBr, in cm$^{-1}$): 530, 564, 614, 689, 728, 764, 828, 929, 993, 1007, 1029, 1121, 1179, 1229, 1443, 1471, 1486, 1514, 1600, 1628, 2557, 2842, 3029.
1H-NMR (ppm): 1.90 (br d, $H_{5eq}$, 1H); 2.10–2.28 (m, $H_{5ax}$, 1H); 2.38–2.52 (m, $H_3$, 1H); 2.82 (ddd, $H_4$, 1H); 3.02–3.18 (m, $H_{2ax}$, $H_{6ax}$, 2H); 3.37 (dd, $H_7$, 1H); 3.48 (d, $H_7$, 1H); 3.60–3.82 (m, $H_{2eq}$, $H_{6eq}$, 2H); 5.87 (s, $H_{7''}$, 2H); 6.06 (dd, $H_{6''}$, 1H); 6.29 (d, $H_{2''}$, 1H); 6.60 (d, $H_{5''}$, 1H); 6.90 (dd, $H_{3'}$, $H_{5'}$, 2H); 7.04 (dd, $H_{2'}$, $H_{6'}$, 2H); 7.40 (d, ArH, 3H); 7.94 (d, SArH, 2H); 8.81 (br d, $NH_{eq}$, 1H); 9.04 (br d, $NH_{ax}$, 1H).
13C-NMR (ppm): 29.9 (s, $C_5$); 39.2 (s, $C_3$); 41.5 (s, $C_4$); 44.8 (s, $C_6$); 47.0 (s, $C_2$); 67.3 (s, $C_7$); 97.9 (s, $C_{2''}$); 101.2 (s, $C_{7''}$); 105.5 (s, $C_{6''}$); 107.8 (s, $C_{5''}$); 115.7 (d, $C_{3'}$, $C_{5'}$); 125.9 (s, $C_b$); 128.6 (s, $C_d$); 128.8 (s, $C_6$, $C_{2'}$); 130.6 (s, $C_{cn}$); 137.1 (s, $C_{4'}$); 141.9 (s, $C_1$); 144.1 (s, $C_g$); 148.2 (s, $C_{3''}$); 153.7 (s, $C_{1''}$); 161.8 (s, $C_{4'}$).

R = p-$CH_3C_6H_4$ (paroxetine p-toluene sulfonate):

m.p.: 148°–150° C.
DSC curve (closed pan, 10° C./min): onset 151.6° C., 71.6 J/g.
IR spectrum (KBr, in cm$^{-1}$): 529, 557, 671, 771, 800, 814, 921, 936, 1000, 1029, 1100, 1157, 1186, 1229, 1471, 1486, 1507, 1600, 2557, 2829, 3029.
1H-NMR (ppm): 1.89 (br d, $H_{5eq}$, 1H); 2.10–2.50 (m, $H_{5ax}$, $H_3$,$CH_2$ 5H); 2.82 (ddd, $H_4$, 1H); 2.97–3.18 (m, $H_{2ax}$, $H_{6ax}$, 2H); 3.36 (dd, $H_7$, 1H); 3.48 (dd, $H_7$, 1H); 3.52–3.77 (m, $H_{2eq}$, $H_{6eq}$, 2H); 5.87 (s, $H_{7''}$, 2H); 6.06 (dd, $H_{6''}$, 1H); 6.28 (d, $H_{2''}$, 1H); 6.59 (d, $H_{5''}$, 1H); 6.90 (dd, $H_{3'}$, $H_{5'}$, 2H); 7.05 (dd, $H_{2'}$, $H_{6'}$, 2H); 7.24 (d, $CH_3$ArH, 2H); 7.83 (d, SArH, 2H); 8.91 (br d, $NH_{eq}$, 1H); 9.17 (br d, $NH_{ax}$, 1H).
13C-NMR (ppm): 21.3 (s, $C_e$); 29.9 (s, $C_5$); 39.2 (s, $C_3$); 41.5 (s, $C_4$); 44.7 (s, $C_6$); 46.9 (s, $C_2$); 67.3 (s, $C_7$); 97.8 (s, $C_{2''}$); 101.1 (s, $C_{7''}$); 105.5 (s, $C_{6''}$); 107.8 (s, $C_{5''}$); 115.6 (d, $C_{3'}$, $C_{5'}$); 125.8 (s, $C_b$); 129.0 (s, $C_6$, $C_{2'}$); 129.1 (s, $C_e$); 137.2 (s, $C_{4'}$); 140.8 (s, $C_d$); 141.5 (s, $C_a$); 141.9 (s, $C_1$); 148.2 (s, $C_{3''}$); 153.8 (s, $C_{1''}$); 161.8 (d, $C_{4'}$).

R = p-$ClC_6H_4$ (paroxetine p-chlorobenzene sulfonate):

mp.: 75°–80° C.
IR spectrum (KBr, in cm$^{-1}$): 486, 557, 643, 736, 821, 1000, 1029, 1086, 1114, 1186, 1229, 1471, 1486, 1514, 1600, 1657, 2857, 3029.
1H-NMR (ppm): 1.91 (br d, $H_{5eq}$, 1H); 2.15 (ddd, $H_{5ax}$, 1H); 2.37–2.52 (m, $H_3$, 1H); 2.81 (ddd, $H_4$, 1H); 2.93–3.21 (m, $H_{2ax}$, $H_{6ax}$, 2H); 3.37 (dd, $H_7$, 1H); 3.49 (d, $H_7$, 1H); 3.61–3.81 (m, $H_{2eq}$, $H_{6eq}$, 2H); 5.88 (s, $H_{7''}$, 2H); 6.05 (dd, $H_{6''}$, 1H); 6.27 (d, $H_{2''}$, 1H); 6.59 (d, $H_{5''}$, 1H); 6.91 (dd, $H_{3'}$, $H_5$ 2H); 7.03 (dd, $H_{2'}$, $H_{6'}$, 2H); 7.39 (d, CLArH, 2H); 7.86 (d, SArH, 2H); 8.78 (br d, $NH_{eq}$, 1H); 9.02 (br d, $NH_{ax}$, 1H).
13C-NMR (ppm): 30.0 (s, $C_5$); 39.3 (s, $C_3$); 41.5 (s, $C_4$); 44.9 (s, $C_6$); 47.1 (s, $C_2$); 67.3 (s, $C_7$); 97.9 (s, $C_{2''}$); 101.2 (s, $C_{7''}$); 105.5 (s, $C_{6''}$); 107.9 (s, $C_{5''}$); 115.8 (d, $C_{3'}$, $C_{5'}$); 127.6 (s, $C_b$); 128.8 (s, $C_6$, $C_{2'}$); 132.0 (s, $C_d$); 137.0 (s, $C_c$); 137.2 (s, $C_{4'}$); 141.8 (s, $C_1$); 142.0 (s, $C_a$); 148.2 (s, $C_{3''}$); 153.6 (s, $C_{1''}$); 161.8 (d, $C_{4'}$).

The compounds of the invention are crystalline, with defined melting points, DSC curves and IR spectra. It cannot be excluded that, under different conditions of their formation and under specific conditions, they could exist also in other crystalline or polymorph modifications which may differ from those as described herein. The compounds of the invention are also generally very stable and non-hygroscopic.

It should be understood that the present invention comprising acid addition salts with organic sulfonic acids are substantially free of the bound organic solvent. Preferably, the amount of bound organic solvent should be less than 2.0% (w/w) as calculated on the anhydrous basis. They nevertheless may contain crystallization water and also unbound water, that is to say water which is other than water of crystallization.

In the following tables 2 and 3, examples of results of hygroscopicity tests and stability tests (in comparison with known salts of paroxetine) are presented.

TABLE 2

Hygroscopicity of certain salts of paroxetine (40° C. 75% rel.hum).

| water content (in %) at | t = 0 | t = 4 weeks |
|---|---|---|
| methane sulfonate | 0.35 | +0.04 |
| p-toluene sulfonate | 0.70 | <0.02 |
| hydrochloride | — | +2.5 |

TABLE 3

Solubility of paroxetine salts in water (in mg/ml)

| | 20° C. | 50° C. |
|---|---|---|
| methane sulfonate | >1000/10 min | 1300 |
| p-toluene sulfonate | >1000 | >1000 |
| hydrochloride hemihydrate | 4.9 | 12.6 |
| hydrochloride anhydrate | 8.2 | 24.2 |

TABLE 4

Stability of paroxetine salts by HPLC (total amount of degradation in %).

| | degradation 20° C. | 80° C. |
|---|---|---|
| methane sulfonate | not observed | <0.2%, 3 months |
| p-toluene sulfonate | not observed | <0.2%, 3 months |
| maleate | 0.2%, 12 months | >50%, 5 days |

TABLE 5

Solubility of salts of paroxetine in nonaqueous solvents (in mg/ml)

| | | methane sulfonate | p-toluene sulfonate |
|---|---|---|---|
| Ethanol | 20° C. | 36 | 50 |
| | 78° C. | 250 | >500 |
| 2-Propanol | 20° C. | 7 | 14 |
| | 82° C. | 330 | >500 |
| Acetone | 20° C. | 5 | 16 |
| | 56° C. | 37 | 125 |
| Ethyl acetate | 20° C. | 2 | 22 |
| | 77° C. | 25 | >500 |
| n-Hexane | 20° C. | <0.05 | <0.05 |
| | 69° C. | 0.05 | <0.05 |

Examples of analytical data of the paroxetine salts and the free base prepared in Examples 5 to 7 are given in Table 6.

TABLE 6

Characterization of salts/free base of paroxetine paroxetine maleate:

m.p.: 128–130° C.
1H-NMR (ppm): 1.65–2.00 (m, $H_{5eq}$, $H_{5ax}$, 2H); 2.00–2.50 (m, $H_3$, 1H); 2.55–3.15 (m, $H_{2ax}$, $H_{6ax}$, $H_4$, 3H); 3.15–3.75 (m, $H_{2eq}$, $H_{6eq}$, $H_7$, 3H); 5.67 (s, $H_{7''}$, 2H); 5.97 (s, $H_a$, 1H); 6.12 (dd, $H_{6''}$, 1H); 6.42 (d, $H_{2''}$, 1H); 6.67 (d, $H_{5''}$, 1H); 6.95–7.35 (m, $H_{2'}$, $H_{3'}$, $H_{5'}$, $H_{6'}$, 4H).

paroxetine acetate:

m.p.: 123–125° C.
1H-NMR (ppm): 1.70–2.00 (m, $H_{5eq}$, $H_{5ax}$, 2H); 1.97 (s, $H_a$, 3H); 2.05–2.50 (m, $H_3$, 1H); 2.50–3.00 (m, $H_4$, $H_{2ax}$, $H_{6ax}$, 3H); 3.05–3.75 (m, $H_{2eq}$, $H_{6eq}$, $H_7$, 3H); 6.05 (s, $H_{7''}$, 2H); 6.28 (dd, $H_{6''}$, 1H); 6.58 (d, $H_{2''}$, 1H); 6.65 (d, $H_{5''}$, 1H); 7.10–7.50 (m, $H_{2'}$, $H_{3'}$, $H_{5'}$, $H_{6'}$, 4H).

paroxetine:

1H-NMR (ppm): 1.60–2.00 (m, $H_{5ax}$, $H_{5eq}$, 2H); 2.00–2.35 (m, $H_3$, 1H); 2.40–2.95 (m, $H_4$, $H_{2ax}$, $H_{6ax}$, 3H); 3.15–3.70 (m, $H_{2eq}$, $H_{6eq}$, $H_7$, 2H); 5.67 (s, $H_{7''}$, 2H); 6.11 (dd, $H_{6''}$, 1H); 6.43 (d, $H_{2''}$, 1H); 6.62 (d, $H_{5''}$, 1H); 6.80–7.35 (m, $H_{2'}$, $H_{3'}$, $H_{5'}$, $H_{6'}$, 4H).

It will be clear that the invention is not limited to the above description, but is rather determined by the following claims.

REFERENCE

Psychopharmacology, 57, 151–153 (1978)]; ibid. 68, 229–233 (1980), European Journal of Pharmacology, 47, 351–358 (1978)]; in U.S. Pat. No. 4,007,196, the preparation of paroxetine maleate is reported.

What is claimed is:

1. A process for preparing paroxetine hydrochloride comprising contacting paroxetine methanesulfonate and hydrochloric acid and thereby forming paroxetine hydrochloride.

2. The process according to claim 1, wherein said paroxetine methane sulfonate is crystalline.

3. The process according to claim 2, wherein said crystalline paroxetine methane sulfonate was prepared by crystallizing paroxetine methane sulfonate from ethyl acetate.

* * * * *